(12) United States Patent
Ouchi et al.

(10) Patent No.: US 7,723,708 B2
(45) Date of Patent: May 25, 2010

(54) OPTICAL SEMICONDUCTOR DEVICE IN WHICH AN ELECTROMAGNETIC WAVE IS GENERATED IN A REGION OF AN APPLIED ELECTRIC FIELD

(75) Inventors: Toshihiko Ouchi, Sagamihara (JP); Takeaki Itsuji, Hiratsuka (JP); Shintaro Kasai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 722 days.

(21) Appl. No.: 10/569,601

(22) PCT Filed: Jul. 28, 2005

(86) PCT No.: PCT/JP2005/014259

§ 371 (c)(1),
(2), (4) Date: Feb. 24, 2006

(87) PCT Pub. No.: WO2006/011668

PCT Pub. Date: Feb. 2, 2006

(65) Prior Publication Data

US 2008/0217538 A1    Sep. 11, 2008

(30) Foreign Application Priority Data

Jul. 30, 2004  (JP)  ............................. 2004-223656
Feb. 1, 2005   (JP)  ............................. 2005-025210

(51) Int. Cl.
    *G21G 4/00*    (2006.01)
(52) U.S. Cl. ..................... 250/493.1; 250/250; 257/431
(58) Field of Classification Search ................. 257/48
    See application file for complete search history.

(56) References Cited

U.S. PATENT DOCUMENTS

| 2,847,386 | A | * | 8/1958 | Mazo et al. | ........... 252/301.6 S |
| 4,626,883 | A | * | 12/1986 | Kash et al. | .................. 333/247 |
| 4,749,550 | A | * | 6/1988 | Goldie et al. | ................. 422/19 |
| 4,751,513 | A | * | 6/1988 | Daryoush et al. | ..... 343/700 MS |

(Continued)

FOREIGN PATENT DOCUMENTS

EP            0 606 776 A2       7/1994

(Continued)

OTHER PUBLICATIONS

Auston, "Ultrafast Optoelectronics," Ultrashort Laser Pulses, vol. 60, 1993, pp. 183-233.*

(Continued)

*Primary Examiner*—Kenneth A Parker
*Assistant Examiner*—Anthony Ho
(74) *Attorney, Agent, or Firm*—Fitzpatrick, Cella, Harper & Scinto (57) ABSTRACT

The present invention provides an optical semiconductor device including a semiconductor thin film (4) having photoconductivity and a pair of electrodes (5) and (10) for applying an electric field to an inside of the semiconductor thin film (4) in a direction approximately vertical to a surface of the semiconductor thin film (4), wherein the semiconductor thin film (4) generates an electromagnetic wave when light is applied to a region thereof to which the electric field is applied. The electrodes are provided to a front surface and a back surface of the semiconductor thin film (4) with the semiconductor thin film interposed therebetween.

7 Claims, 8 Drawing Sheets

U.S. PATENT DOCUMENTS

| | | | | |
|---|---|---|---|---|
| 5,055,810 | A * | 10/1991 | de La Chapelle et al. | 333/262 |
| 5,194,979 | A * | 3/1993 | Koai et al. | 398/202 |
| 5,227,621 | A * | 7/1993 | Kim et al. | 250/214.1 |
| 5,283,564 | A * | 2/1994 | Katakura et al. | 345/87 |
| 5,323,024 | A * | 6/1994 | Adams | 257/80 |
| 5,341,017 | A * | 8/1994 | Booth et al. | 257/459 |
| 5,351,063 | A * | 9/1994 | Kim et al. | 343/895 |
| H001443 | H * | 6/1995 | Kim et al. | 252/582 |
| 5,675,295 | A * | 10/1997 | Brebels et al. | 331/105 |
| 5,701,325 | A | 12/1997 | Ouchi et al. | 372/96 |
| H001717 | H * | 4/1998 | Stoudt et al. | 257/431 |
| 5,789,750 | A * | 8/1998 | Nuss | 250/338.1 |
| 5,850,408 | A | 12/1998 | Ouchi et al. | 372/27 |
| 5,912,455 | A * | 6/1999 | Pocholle et al. | 250/214 R |
| 6,046,096 | A | 4/2000 | Ouchi | 438/510 |
| 6,055,251 | A * | 4/2000 | Ouchi et al. | 372/28 |
| 6,089,442 | A | 7/2000 | Ouchi et al. | 228/180.1 |
| 6,222,868 | B1 | 4/2001 | Ouchi et al. | 372/50 |
| 6,320,691 | B1 | 11/2001 | Ouchi et al. | 359/237 |
| 6,407,708 | B1 * | 6/2002 | Jasper, Jr. | 343/701 |
| 6,476,596 | B1 * | 11/2002 | Wraback et al. | 324/158.1 |
| 6,477,286 | B1 * | 11/2002 | Ouchi | 385/14 |
| 6,507,594 | B1 | 1/2003 | Furukawa et al. | 372/36 |
| 6,771,677 | B2 | 8/2004 | Furukawa et al. | 372/36 |
| 6,836,579 | B2 | 12/2004 | Ouchi | 385/14 |
| 6,970,612 | B2 | 11/2005 | Ouchi | 385/14 |
| 7,027,668 | B2 * | 4/2006 | Tavlykaev et al. | 385/2 |
| 7,236,293 | B2 * | 6/2007 | Bae | 359/326 |
| 7,619,263 | B2 * | 11/2009 | Shur et al. | 257/198 |
| 2005/0215031 | A1 * | 9/2005 | Ouchi | 438/459 |
| 2005/0233490 | A1 | 10/2005 | Kasai et al. | 438/46 |
| 2006/0056757 | A1 | 3/2006 | Ouchi | 385/14 |

FOREIGN PATENT DOCUMENTS

| | | |
|---|---|---|
| GB | 2392779 A * | 3/2004 |
| JP | 10-104171 | 4/1998 |
| JP | 10-104174 | 4/1998 |
| JP | 2004-22766 | 1/2004 |
| JP | 2004-101257 | 4/2004 |
| JP | 2004-172410 | 6/2004 |

OTHER PUBLICATIONS

M. Nagel et al., "Integrated THz Technology for Label-free Genetic Diagnostics", Appl. Phys. Lett., vol. 80, No. 1, pp. 154-156, Jan. 7, 2002.

L. Desplanque et al., "Generation and Detection of Terahertz Pulses Using Post-process Bonding of Low-temperature-grown GaAs and AlGaAs", Appl. Phys. Lett., vol. 84, No. 12, pp. 2049-2051, Mar. 22, 2004.

* cited by examiner

OPTICAL SEMICONDUCTOR DEVICE IN WHICH AN ELECTROMAGNETIC WAVE IS GENERATED IN A REGION OF AN APPLIED ELECTRIC FIELD

TECHNICAL FIELD

The present invention relates to an optical semiconductor device functioning as a device for generating and detecting a high frequency electromagnetic wave mainly in a region from a millimeter wave to a terahertz wave using light irradiation.

BACKGROUND ART

In recent years, there has been developed a nondestructive sensing technique using an electromagnetic wave (30 GHz to 30 THz) ranging from a millimeter wave to a terahertz (THz) wave. Techniques under development in the application field of the electromagnetic wave having this frequency band include a technique for carrying out imaging using a safe radioscopic inspection system in place of an X-ray system, a spectroscopic technique for obtaining an absorption spectrum or a complex dielectric constant of the inside of a substance to evaluate a coupling state of atoms, a technique for analyzing a biomolecular, and a technique for evaluating concentration or mobility of carriers.

Figure 10:
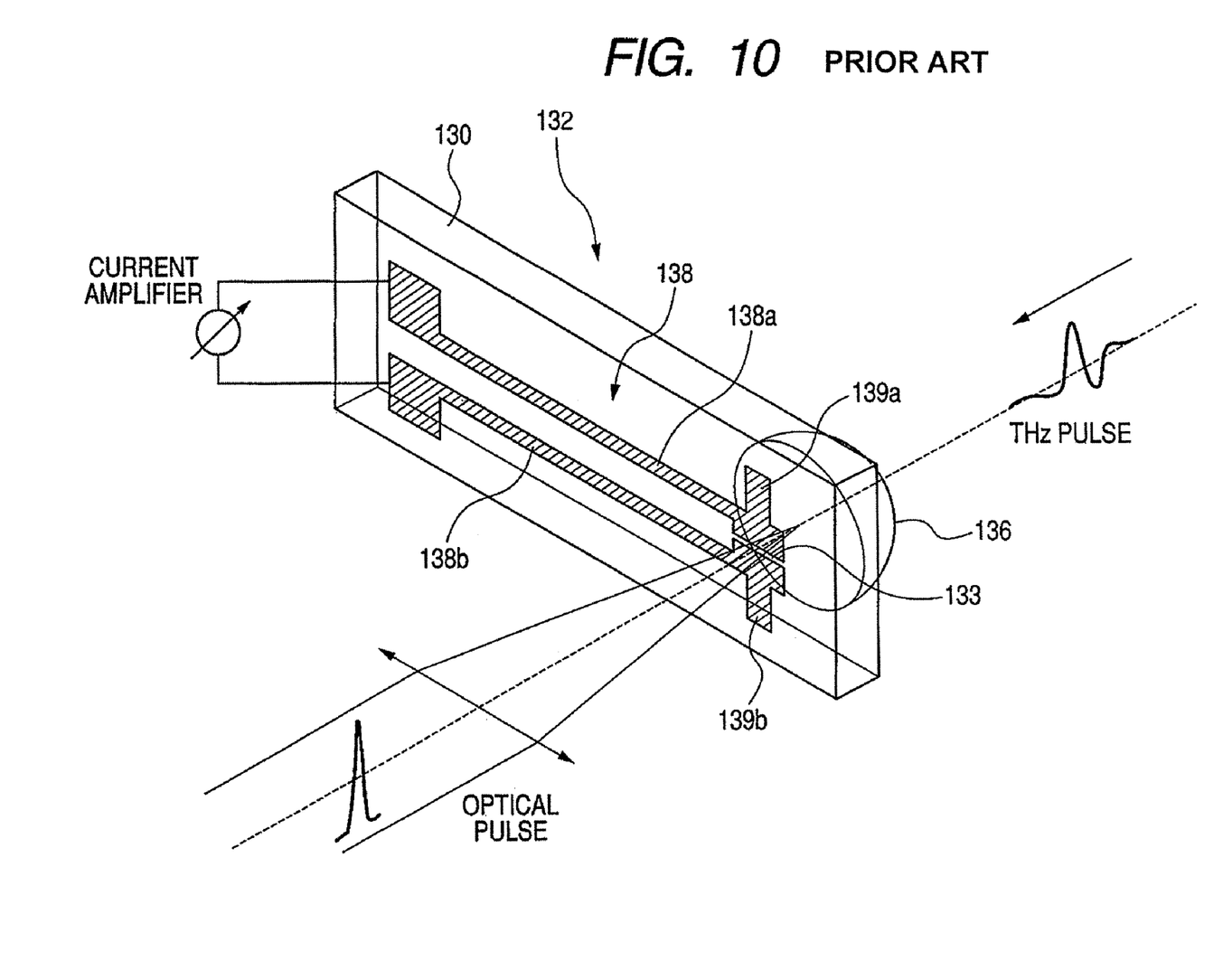
FIG. 10 shows a conventional photoconductive element.

JP10-104171A discloses a THz generating means suitably employing a photoconductive element in which an antenna also serving as an electrode is provided on a photoconductive film deposited on a substrate. A detector 132 is shown in FIG. 10 as an exemplary structure of the photoconductive element. A substrate 30 has, for example, a silicon-on-sapphire structure treated with radiation, in which a silicon film as a photoconductive material is deposited on a sapphire substrate. Generally, LT-GaAs grown at a low temperature on a GaAs substrate is also often used as a photoconductive film. A dipole antenna 138 formed on a surface includes a pair of dipole feed lines 138a and 138b and a pair of dipole arm portions 139a and 139b. An optical pulse is condensed at a gap 133. When a voltage is applied across the gap, a THz pulse is generated. When photocurrent is detected without applying a voltage, a THz pulse can be detected. A substrate lens 136 serves to couple a slab mode (substrate mode) of an electromagnetic wave confined in a substrate 130 to a free-space radiation mode and also serves to control an angle of radiation in the electromagnetic wave space-propagation mode.

The foregoing illustrates by way of example that a photoconductive element is used alone to propagate an electromagnetic wave into space. On the other hand, Applied Physics Letters, vol. 80, no. 1, Jan. 7, 2002, pp. 154-156 and Applied Physics Letters, vol. 84, no. 12, Mar. 22, 2004, pp. 2049-2051 disclose a small functional device in which a semiconductor film functioning as a photoconductive element and a transmission path for transmitting a generated electromagnetic wave are integrated on a single substrate. This device has such a structure that a thin film of only an epitaxial layer of a photoconductive element made of LT-GaAs is transferred on a portion of a high frequency transmission path formed on a substrate. According to Applied Physics Letters, vol. 80, no. 1, Jan. 7, 2002, pp. 154-156, a microstrip line is formed on an Si substrate with an insulator resin interposed. A gap is formed at a portion of the line. An LT-GaAs thin film is arranged only at the bottom of the gap. On the other hand, according to Applied Physics Letters, vol. 84, no. 12, Mar. 22, 2004, pp. 2049-2051, coplanar strip lines are formed on a quartz substrate. An LT-GaAs thin film is partially arranged to extend across a gap between the two lines.

Each device performs driving so that a laser beam is applied, through spatial propagation, to the gap of the metal line from the surface side of the substrate to allow a generated THz electromagnetic wave to propagate through the line.

DISCLOSURE OF THE INVENTION

In the integrated device discussed above, it is difficult to improve coupling efficiency and to maintain stability because a laser beam is aligned with a photoconductive element by spatial coupling. Since the gap portion of the photoconductive element is formed on the substrate surface, it is impossible to apply light laterally. Thus alignment-free cannot be achieved by providing an optical waveguide on a substrate. In other words, there remain problems to be solved such as sensitivity in sensing, a total measurement time, and manufacturing costs.

Furthermore, since an electric field is applied through a surface electrode, an internal electric field of LT-GaAs is not uniform and the behavior of a carrier excited by a laser beam cannot be controlled efficiently. In addition, in terms of gap spacing, accurate photolithography is required to form a narrow gap of 1 μm or less with high reproductivity for controlling electric field intensity, thereby leading to an increase in manufacturing cost. Not only an integrated device but also a single photoconductive element allowing an electromagnetic wave to propagate through space has a similar problem.

The present invention provides a photoconductive element as well as an integrated device including such element and a THz-transmission path etc., in which a gap spacing between electrodes and an electric field across the gap can easily be controlled with a simple structure. There is also provided a structure for improving and stabilizing coupling efficiency in coupling with light to be applied to the gap portion.

The present invention provides an optical semiconductor device including a semiconductor thin film having photoconductivity and a pair of electrodes for applying an electric field to an inside of the semiconductor thin film in a direction approximately vertical to a front surface of the semiconductor thin film, wherein the semiconductor thin film receives light in a region thereof to which the electric field is applied to generate an electromagnetic wave.

Furthermore, the present invention provides a sensing device including an electromagnetic wave generating means having a semiconductor thin film having photoconductivity and a pair of electrodes for applying an electric field to an inside of the semiconductor thin film in a direction approximately vertical to a surface of the semiconductor thin film for receiving light in a region thereof to which the electric field is applied to generate an electromagnetic wave and an electromagnetic wave detecting means for detecting an electromagnetic wave, wherein a change in a propagation state of an electromagnetic wave due to an object in a transmission path for an electromagnetic wave is sensed to obtain information on a state of the object.

According to an optical semiconductor device of the present invention, a photoconductive element can be provided in which a gap spacing between electrodes and an electric field across the gap can be controlled with a simple structure. In addition, a structure can be provided which improves and stabilizes coupling efficiency in coupling with light to be applied to the gap portion. In view of the foregoing, there can be provided a terahertz sensing device capable of operating at a low voltage, in a small size, with a sensing optical system being easily adjustable, and with high stability and S/N ratio. Using this sensing device, it is possible to perform analysis of a biological material, an organic substance, or a semiconductor material, noninvasive and noncontact sensing of human body, sensing of a positional change of an object, and the like, at a low cost with high sensitivity.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

BEST MODE FOR CARRYING OUT THE INVENTION

The present invention is characterized, in that an electric field is applied to the inside of a semiconductor thin film in a direction approximately vertical to a surface of the semiconductor thin film. It is particularly preferable that electrodes or quasi-electrodes are formed on a front surface and a back surface of a semiconductor thin film with the semiconductor thin film as a photoconductive film interposed therebetween so that a voltage can be applied in a direction of a film thickness. In an exemplary manufacturing method for implementing this structure, preferably, an electrode is formed on a photoconductive film formed on a first substrate, and thereafter the photoconductive film is left while being bonded to a second substrate, and the first substrate is removed. An electrode or an electromagnetic wave transmission line also serving as an electrode is then formed on the surface, thereby resulting in a photoconductive element formed on the second substrate.

The electromagnetic wave generated at the photoconductive element can be transmitted as it is to the electromagnetic wave transmission path also serving as an electrode. The transmission path may be provided with an antenna for radiation into space. Alternatively, the photoconductive element of the same structure may be used as a THz detector. The electromagnetic wave propagating through the antenna and the transmission path can be led to the THz detector efficiently. A detecting portion and a generating portion for the electromagnetic wave may be connected to each other through the electromagnetic wave transmission path and be integrated on the same substrate.

Furthermore, an optical waveguide may be integrated so that light is coupled from the side surface of the photoconductive element to which a voltage can be vertically applied. A beam for photoexcitation may be transmitted through an optical fiber which may be fixed to the optical waveguide in alignment. A highly stable THz generator/detector is thereby provided without adjustment to the optical system.

The semiconductor thin film to which a voltage can be vertically applied may be of a single composition or may have a multi-layer structure. Specifically, a III-V group semiconductor thin film made of a III-V group compound is preferable. In the case of the single composition, for example, LT-GaAs grown at a low temperature (200° C. to 300° C.) using a molecular beam epitaxy method is suitably used. The distance between the electrodes can be controlled by the thickness of the epitaxially-grown film, so that electric field intensity can be set with high reproductivity and with high precision. In the case of the multi-layer structure, a heterojunction structure is formed to sandwich a light absorption layer, which is reduced to about 100 nm in thickness and is adequately doped, between semiconductor layers with a wide band gap, thereby achieving both high mobility and short life of carriers. The present invention is not limited thereto, and semiconductors different in type of conduction or energy band can be layered. As described above, the gap to which an electric field is applied is controlled in nano-order by controlling a thickness of an epitaxial film, so that the problem with surface treatment can be solved in terms of reproductivity, costs, and the like.

The embodiments of a photoconductive element and an integrated device including the same will be described as an optical semiconductor device for generating and detecting the terahertz. The material, structure, device, and the like are not limited to the illustration provided herein. Furthermore, a variety of applications of the element and of characteristics of the generated electromagnetic wave may be employed in addition to the illustration given here.

First Embodiment

Figure 1:
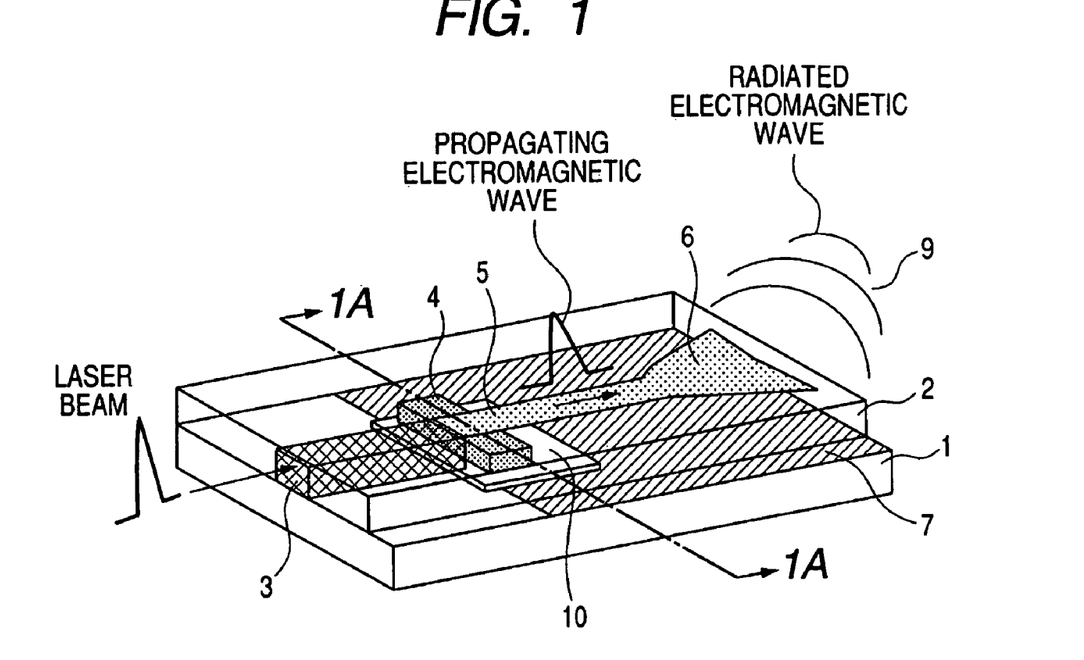
FIG. 1 is a structural view of an integrated device according to a first embodiment of the present invention.

According to a first embodiment of the present invention, an optical waveguide, a microstrip line, and a photoconductive element for converting light into a terahertz electromagnetic wave are integrated on the same substrate, as shown in FIG. 1.

A Ti/Au electrode (or an Al electrode) 7 serving as a ground plane is formed in a partial region on an Si substrate 1. A low-temperature (LT)-grown GaAs epitaxial film 4 having a thickness of 2 µm is transferred in the vicinity of the center. An optical waveguide 3 is formed on the left side of the LT-GaAs such that an externally-incoming beam efficiently performs photoirradiation to the side surface of the LT-GaAs film. On the other hand, a microstrip line 5 of Ti/Au is formed on the right side on the top with an insulator 2 interposed such that an electromagnetic wave generated at LT-GaAs can propagate. This line also serves as an upper electrode of LT-GaAs. A patch antenna 6 is formed on the other end portion of the line such that an electromagnetic wave 9 can radiate through space. This antenna is a wide-band type, having a tapered shape in order to emit a pulse waveform efficiently.

Figure 1A:
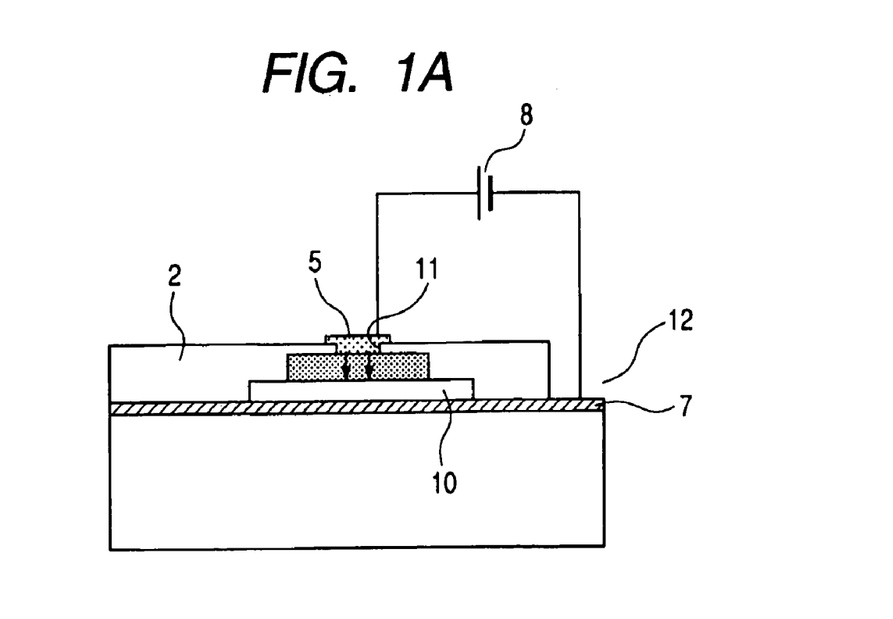
FIG. 1A is a cross-sectional view taken along 1A-1A of FIG. 1.

Referring to a cross sectional view (FIG. 1A) taken along 1A-1A of FIG. 1, an insulator 2 has an open window 11 only at the top of LT-GaAs for obtaining electrode contact. The right-side end portion of the insulator 2 is provided with a cutout portion 12 for obtaining a terminal for applying a voltage 8 to LT-GaAs. An AuGe/Ni/Au electrode 10 for making a contact with LT-GaAs is fused with Au of the top surface of a ground plane 7 using AuSn solder (not shown).

The aforementioned configuration allows a photoconductive element to operate with application of a uniform electric field in a direction vertical to the film thickness of LT-GaAs, as shown in FIG. 1. Furthermore, the gap spacing can be defined by the thickness of the epitaxial film, thereby achieving high accuracy and reproducibility. Typically, the substrate has a size as small as about 1 cm square as a whole. Although the optical waveguide has a cross section about 10 µm square, it may be increased in size to 50 µm square at the beam incoming portion in order to improve the coupling efficiency. Conversely, it may be reduced to 2 µm in the thickness direction in the vicinity of the point for irradiation to LT-GaAs and tapered for adjusting the size (not shown). The microstrip line has a width of 15 µm. When the transferred LT-GaAs is driven as a photoconductive element, the width of the upper electrode is defined as 10 µm by an insulator window 11. Benzocyclobutene (BCB), polysilane, or polyimide is suitably used as an insulator, which is easily processed and has a low dielectric loss at a high frequency. The thickness is set to approximately 6 µm. The size or the material illustrated above is only by way of example and the present invention is not limited thereto.

Although a patch antenna is used as an antenna by way of example, a dipole antenna, a spiral antenna, an F-antenna, or the like may be used. Furthermore, a slot antenna or a bow-tie antenna of a surface-type may be used by converting the transmission line to a slot line or a coplanar line. Alternatively, a Yagi antenna, a horn antenna, or the like may be integrated for controlling directivity.

Referring now to FIGS. 2A, 2B, 2C, 2D, 2E and 2F, a process for manufacturing the device of this embodiment will be illustrated. The same components as in FIG. 1 will be denoted by the same number. It should be noted that FIGS. 2BT, 2DT, 2ET, and 2FT are the top views of FIGS. 2B, 2D, 2E, and 2F, respectively.

Figure 2:
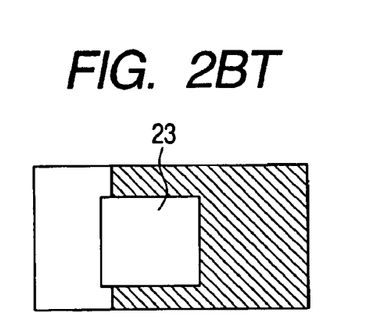
Figure 2A:
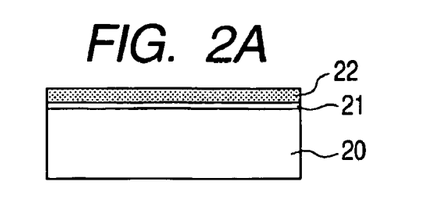
FIGS. 2A, 2B, 2C, 2D, 2E and 2F illustrate a method of manufacturing an integrated device, and FIGS. 2BT, 2DT, 2ET, and 2FT are top views of FIGS. 2B, 2D, 2E, and 2F, respectively.

In FIG. 2A, an AlAs layer 21 of 100 nm serving as a sacrifice layer for removing the substrate and an LT-GaAs layer 22 of 2 µm grown at a low temperature of 250° C. are grown on a GaAs substrate 20 by a molecular beam epitaxy (MBE) method or the like.

Figure 2B:
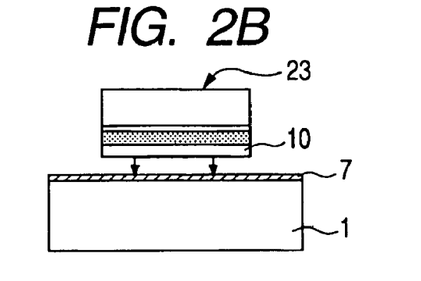

In FIG. 2B, an AuGe/Ni/Au electrode 10 is formed on the LT-GaAs surface and is alloyed at 40° C. Mechanical polishing is performed on the GaAs substrate 20 to 120 µm, resulting in a chip 23 of about 200 µm square. Additionally, in order to increase the thickness of the chip, the electrode 10 may be Au-plated to have a thickness of 3 µm. An AuSn solder is formed in a partial region of the ground plane 7 formed beforehand on an Si substrate 1. The chip 23 is handled to lie on a desired position and is then fused by heating. When Au-plating is performed on the chip side, Sn may subsequently be provided through plating or deposition on the surface. Chips may be handled one by one using electrostatic tweezers or the like. Alternatively, on a wafer level, a plurality of chips may be temporarily bonded at a required spacing on a glass substrate or the like and then subjected to fusion collectively.

Figure 2C:
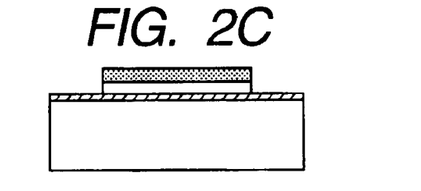

In FIG. 2C, the GaAs substrate of the fused chip is to be removed. In this case, while the surroundings of chip 23 are covered with an organic material or the like, GaAs is etched using a mixed solution of hydrogen peroxide and ammonia at a rate of 10 µ/min. The etching then stops at the AlAs layer. The AlAs serving as a sacrifice layer is removed using concentrated hydrochloric acid.

Figure 2D:
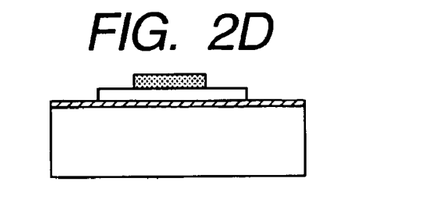

In FIG. 2D, photolithography and wet-etching in the similar manner as described above are performed in order to reduce the size of the transferred LT-GaAs to 10 µm×50 µm. This etching also aims to remove a damage layer of an LT-GaAs sidewall. Here, a portion 25 of the electrode 10, which is left after etching GaAs, may be removed by performing metal etching.

Figure 2E:
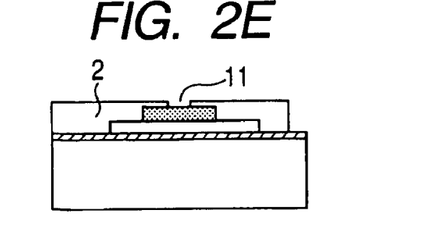

In FIG. 2E, an optical waveguide 3 and an insulator 2 for a microstrip line are manufactured through BCB application and photolithography. The optical waveguide 3 is embedded by first forming a core layer using a photosensitive BCB and then applying a non-photosensitive BCB on the whole. The photosensitive BCB having a refractive index higher than that of the non-photosensitive BCB serves as an optical waveguide. After the whole surface is planarized by the non-photosensitive BCB, the window 11 for the electrode of LT-GaAs is formed through photolithography and through reactive ion etching (RIE) using a mixture gas of oxygen and $CF_4$.

Figure 2F:
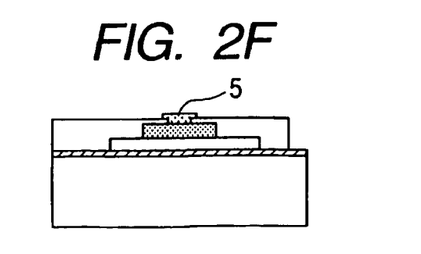

In FIG. 2F, a Ti/Au electrode serving as an upper electrode of LT-GaAs as well as a microstrip. line and an antenna are formed by the lift-off method.

In the foregoing description, BCB is used by way of example. Polyimide may also be used similarly for manufacture. Alternatively, in a method using a photosensitive polysilane, an optical waveguide may be manufactured by changing a refractive index through control of a degree of polymerization using exposure.

Figure 3:
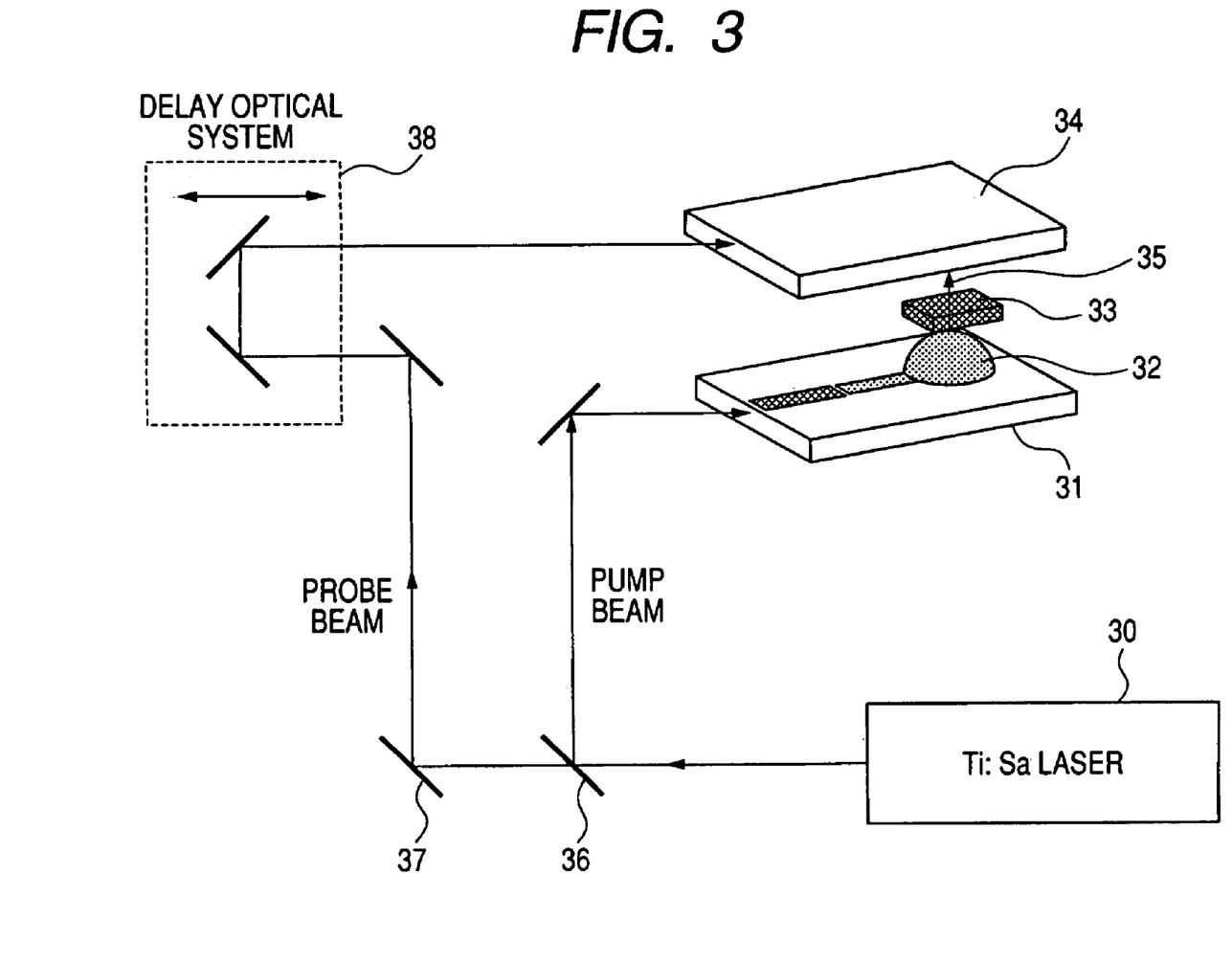
FIG. 3 shows a driving optical system of the integrated device according to the present invention.

FIG. 3 illustrates a driving system of an integrated, vertical electric field application type photoconductive element in accordance with the present invention. When a THz pulse is used as a generation electromagnetic field, an ultra-short pulse of about 100 fsec is generated by a titanium sapphire femto-second laser 30 and is divided into a pump beam and a probe beam using a half mirror 36. The pump beam is coupled to a beam-incoming end of an integrated device 31 according to the present invention to generate a THz electromagnetic wave 35. A hemispherical lens 32 for improving beam directivity is bonded on the upper portion of the antenna emitting an electromagnetic wave. The THz electromagnetic wave pulse passes through an object 33 to be inspected and is received at the antenna of an integrated device 34 on the detection side (facing backwards). The integrated device 34 may have the same structure as that of the device 31 on the generation side. For use as a detector, current flowing between the electrodes of the photoconductive element is detected without application of an electric field. An electromagnetic wave pulse waveform can be obtained without the need for a high-speed electronic circuit by adjusting timing for probe beam to enter at a delay optical system 38. Physical properties and the like of a specimen 33 can be inspected by measuring an amplitude change, a relative propagation delay, a Fourier spectrum change, or the like through waveform analysis. Generally, the intensity of the laser beam is approximately several mW on average with a repetition of about 80 MHz, and an applied voltage for the photoconductive element is about 10 V. In the case of vertical voltage application in accordance with the present invention, the gap spacing is 2

μm, which is less than 5 μm of the commonly-used surface electrode type. Therefore, an applied voltage for obtaining the same electric field intensity can be reduced.

A variety of objects including an organic material, a semiconductor material, a living material, and the like can be inspected in a nondestructive and noncontact manner. An image of distribution can also be obtained by scanning an object two-dimensionally.

It is also possible to perform identification of the state of skin, bloodstream (for example, blood pulse), blood components and the like, as well as personal authentication through detection of a blood vessel pattern or a fingerprint by inserting a human fingertip into an electromagnetic wave propagating path.

Additionally, the present invention is also effective for a radioscopic inspection of a thickness of an inserted object, the count of sheets, or the inside of paper or plastic.

This embodiment as described above provides a semiconductor device in which a vertical electric field application type photoconductive element composed of LT-GaAs is integrated with a microstrip line, an antenna, and an optical waveguide. However, a photoconductive element alone may also operate as an electromagnetic wave generating element, as a matter of course. In such a case, a beam may be applied from the side surface or may be applied from the top in the vicinity of the upper electrode. The upper electrode may be shaped like an antenna in order to increase radiation efficiency.

Although the GaAs group is illustrated here, the other semiconductor such as InP or InAs may be used. Alternatively, an organic semiconductor having photoconductivity may be used.

Second Embodiment

Figure 4:
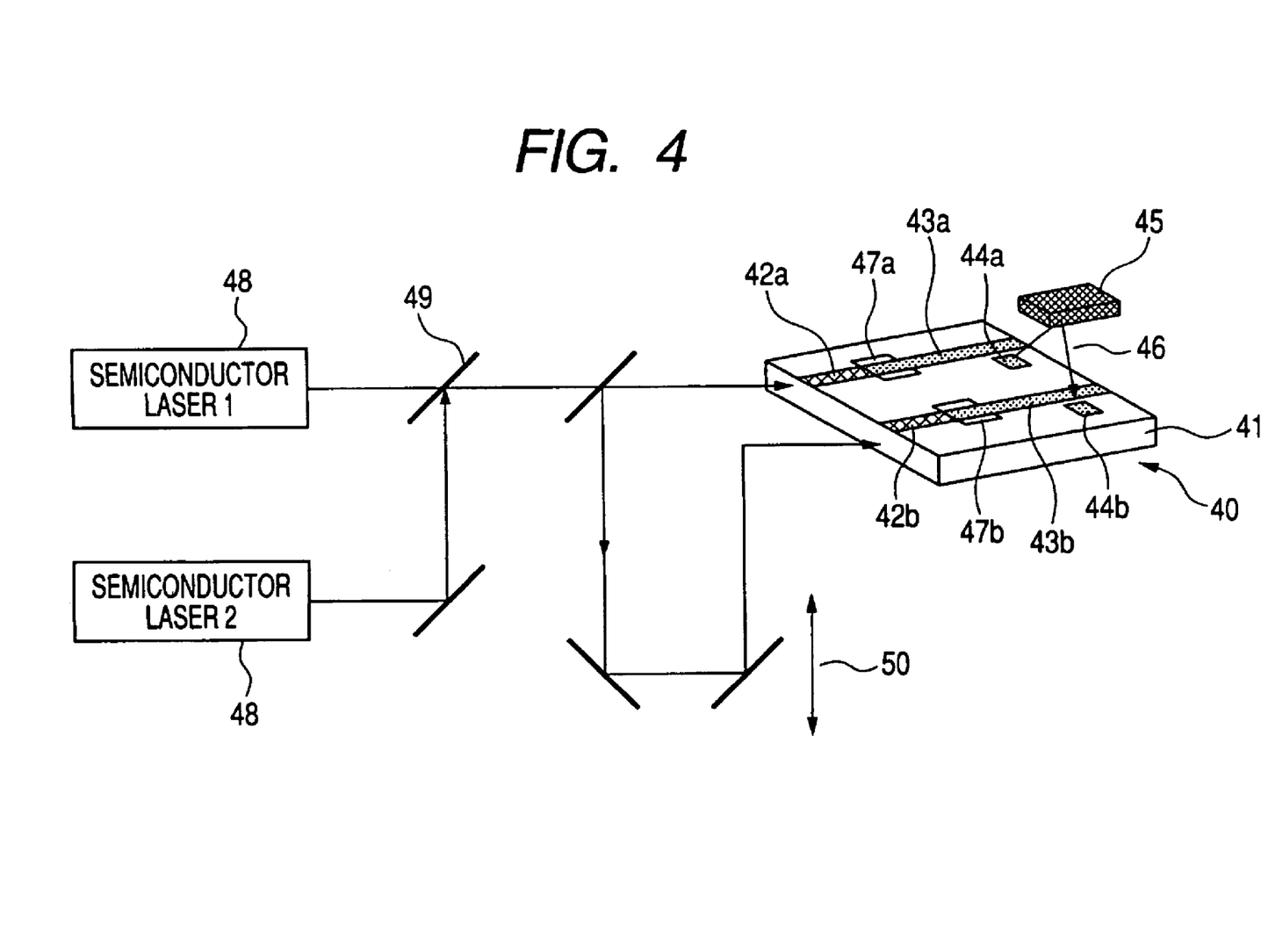
FIG. 4 shows a configuration of an integrated device and a driving system according to a second embodiment of the present invention.

According to a second embodiment of the present invention, a plurality of elements are arrayed on the same semiconductor substrate as shown by an integrated device 40 in FIG. 4. In the manufacturing process shown in the first embodiment, the elements are formed on an Si substrate 41 collectively on a wafer level, so that arrayed elements can be provided freely depending on the arrangement of the element or how the wafer is cut.

More specifically, two optical waveguides 42a and 42b, photoconductive elements 47a and 47b, microstrip lines 43a and 43b, and print dipole antennas 44a and 44b are arrayed in parallel. Although the array spacing is illustrated as 1 cm herein, the present invention is not limited thereto. In this case, a THz electromagnetic wave includes a component propagating through space as shown by an arrow 46, so that the changing state of the electromagnetic wave reflected on an object 45 can be detected.

In terms of an optical system, while a femto-second laser may be used as shown in the first embodiment, two semiconductor lasers 48 are used here in order to reduce the cost and size. When two semiconductor lasers are slightly different in oscillation wavelength in single-mode oscillation, a coupler 49 mixes laser beams to be applied to an input end of the optical waveguide 42a, so that the photoconductive element 47a can generate an electromagnetic wave corresponding to a difference frequency (beat) component. The oscillation frequency of the THz electromagnetic wave of CW can be changed in a range of about 0.1 THz to 3 THz by changing the amount of the difference frequency while being stabilized. On the reception side, on incidence to the optical waveguide 42b through a time adjuster 50, the photoconductive element 47b uses its photomixing function to detect the intensity of the electromagnetic wave received by the antenna 44b. The time adjuster 50 performs a phase adjustment of photomixing. Detection conducted while changing the beat frequency allows a reflection spectrum of an object to be measured for identification of physical properties as in the first embodiment.

Using the reflection measurement, physical properties of a material with a relatively large absorption, a film thickness thereof, a state of surface roughness thereof, or the like can be detected. Considering the use for human beings, it is possible to inspect a state of skin surface such as roughness or a state of aging, a state of pores, a moisture content, collagen, a fat distribution, bloodstream, or a substance in blood.

Alternatively, a positional change of the object 45 can also be sensed by measuring a delay time of a reflected electromagnetic wave. In this case, the semiconductor laser is modulated at a triangular wave of several tens of MHz for positional identification using a THz electromagnetic wave according to the known FMCW method, resulting in a remote position-sensing device with a high resolution (<100 μm).

FIG. 4 shows an optical system symbolically. When a laser beam source does not provide an ultra-short pulse, however, an optical fiber is used for propagation, which is superior in terms of efficiency and space. Coupling with the integrated device can be realized by direct butt coupling, by interposing a lens, or by providing and fixing a pigtail at a fiber tip end in an aligned manner with increased coupling. efficiency, thereby reducing the overall size of the device including a light source. Instead of a combination with a fiber system, a semiconductor laser may be mounted on a planar optical circuit on an Si substrate and be integrated with an integrated device with a photoconductive element thereon.

Third Embodiment

Figure 5:
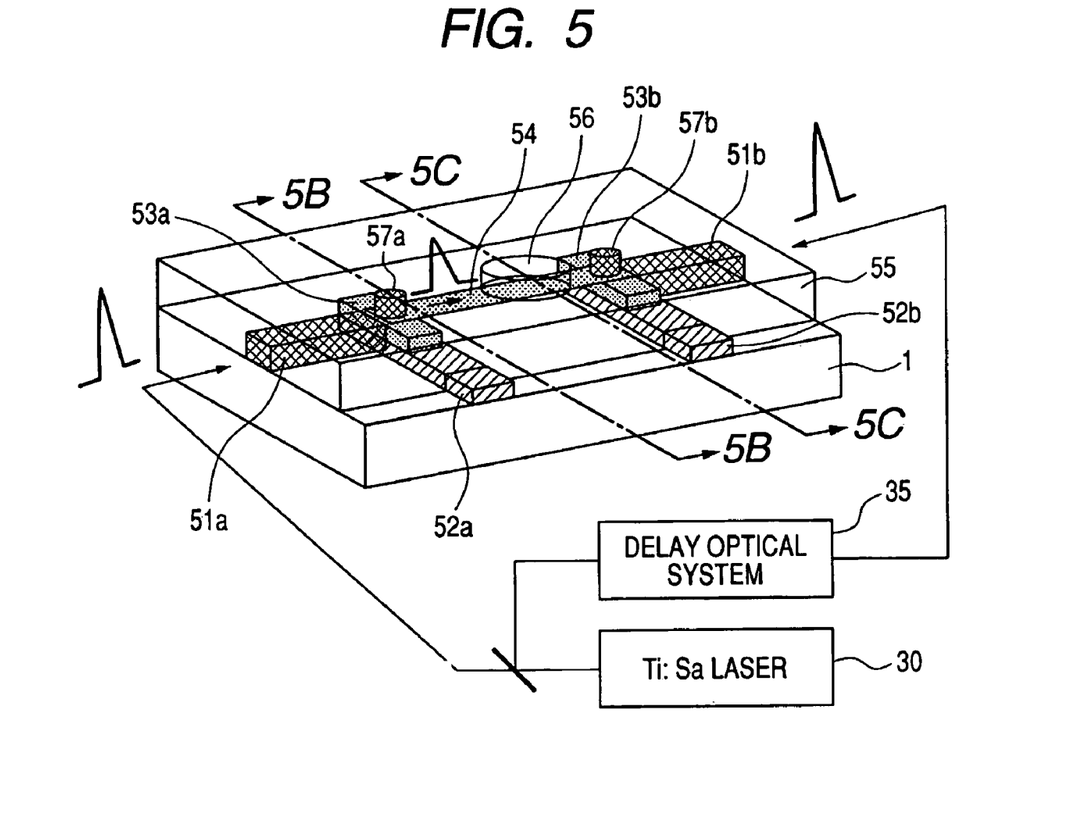
FIG. 5 is a structural view of an integrated device according to a third embodiment of the present invention.

According to a third embodiment of the present invention, as shown in FIG. 5, two photoconductive elements are integrated on the same substrate. This allows a sensor device to function on one substrate for sensing an object placed closely on a high frequency transmission line.

A photoconductive element 53a is similar to that in the first embodiment in that, with application of a vertical electric field between a line 54 and a lower electrode 52a, a THz electromagnetic wave, which is excited by light propagating through an optical waveguide 51a, propagates through the line 54. In this embodiment, a ground plane is not provided, and a high frequency transmission line is a single line including the signal line 54 embedded in an insulator 55 upward and downward. Electrodes 52a and 52b are isolated, each having a thickness of about 3 μm with Au plating for adjusting the height of the photoconductive element.

Figure 5B:
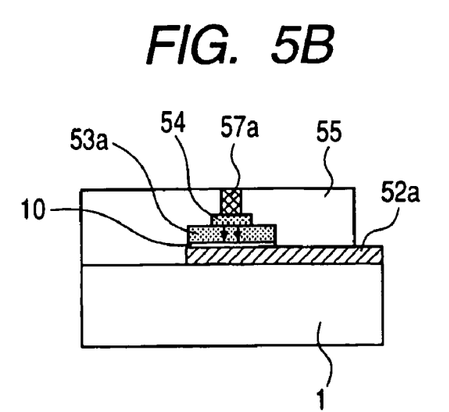
FIGS. 5B and 5C are cross-sectional views taken along 5B-5B and 5C-5C of FIG. 5 respectively.
Figure 5C:
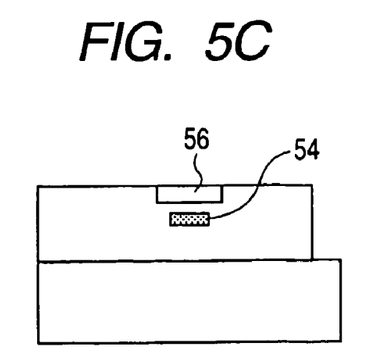

Therefore, the manufacturing process is almost the same as in the first embodiment except that the electrodes 52a and 52b on the side of the Si substrate 1 are patterned and increased in thickness, and that the transmission line 54 also serving as an electrode is formed and then coated with the same insulator on the top by about 3 μm. This is easily understood with reference to the cross sectional view taken along 5B-5B (FIG. 5B) and the cross sectional view taken along 5C-5C (FIG. 5C). As shown in the cross sectional view along 5B-5B, since the insulator 55 is embedded after formation of the line 54, a via electrode 57a is provided for obtaining electrode contact. Furthermore, as shown in the cross sectional view along 5C-5C, the middle portion of the transmission line is provided with a hole 56 for increasing penetration of the propagating electromagnetic wave. A material to be inspected is placed in this hole to be detected efficiently.

An external optical system is similar to that in the first embodiment in that a pump beam from a titanium sapphire femto-second laser is introduced to the THz electromagnetic wave generating side waveguide 51a, while a probe beam is introduced through a delay optical system to a detection side waveguide 51b.

In this system, a change of a propagation state on the transmission line 54 is detected at a photoconductive element 53b so that an object on the transmission path can be identified. At the photoconductive element 53b on the detection side, the generated photocurrent may be measured without application of an electric field, as in the first embodiment.

An electromagnetic wave penetrates as an Evanescent wave into the hole 56 containing a sample, and the propagation state changes depending on the property of the contained object. Specifically, attenuation of an electromagnetic wave, absorption of a specific frequency component, or a propagation delay occurs as a signal change. This leads to a significant size reduction, as compared with the conventional measurement using a spatial optical system, a reduced number of components, improved stability and light coupling efficiency, and an increased S/N ratio.

In addition, liquid, powder, or the like, which are conventionally unmeasurable, is only placed in the hole 56 to be measured. For example, a material of biological origin such as amino acid, DNA, or protein should be measured in a solution for analysis. The present invention provides a biosensor which performs evaluation using a high frequency dielectric property in a state of solution, which has been conventionally difficult.

It should be noted that although a femto-second laser is illustrated as an optical system, a semiconductor laser and an optical fiber can be used to reduce the overall device size, as shown in the second embodiment.

Fourth Embodiment

According to a fourth embodiment of the present invention, there is provided a structure that allows a field intensity to increase and also allows electrons to move at a high speed.

Figure 6:
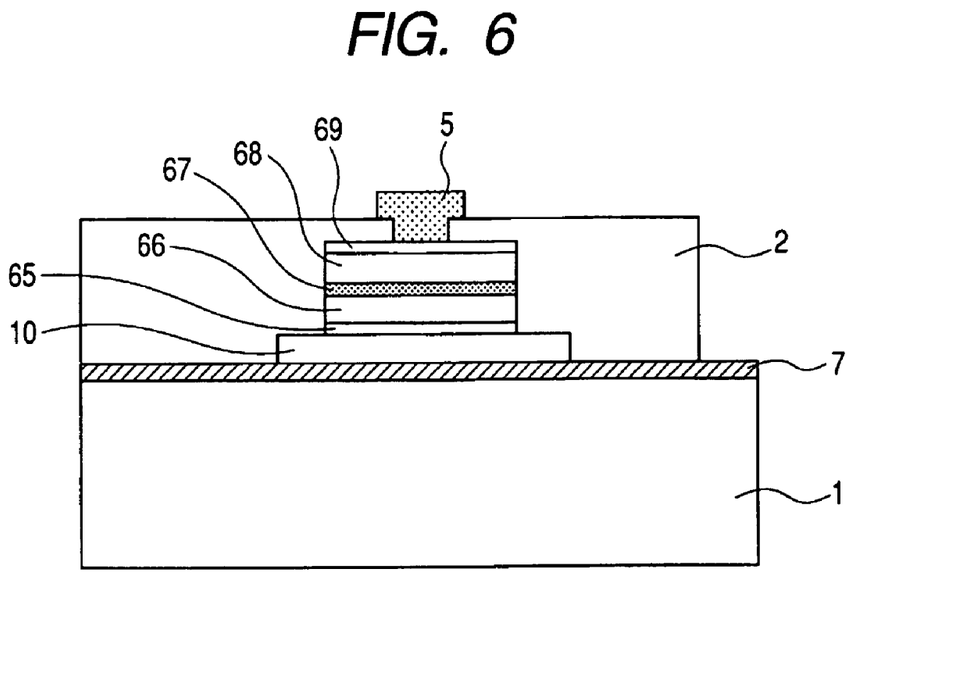
FIG. 6 is a cross sectional view of a photoconductive element portion according to a fourth embodiment of the present invention.

FIG. 6 is a cross sectional view of a photoconductive element portion of an integrated device similar to that in the first embodiment. The structure is the same except the photoconductive element, in which the transferred epitaxial film has a multi-layer film structure. There are shown n-type Al0.08 Ga0.92 As denoted by '65', n-type Al0.2 Ga0.8 As denoted by '66', undoped GaAs denoted by '67', n-type Al0.08 Ga0.92 As denoted by '68', and n-type Al0.2 Ga0.8 As denoted by '69', which are grown at a normal growth temperature (about 600° C.). The n-type layer is highly doped. Specifically, '65' and '69' make electrode contacts with low absorption at an excitation light of 800 nm. In order to attain a total thickness of approximately 2 µm, '66' and '68' are made to have a thickness of 1 µm and the others are made to have a thickness of 100 nm. The absorption of excitation light occurs at the undoped GaAs absorption layer 67 having a thickness of 100 nm, so that the produced carrier can run fast while hardly colliding with a lattice. This embodiment employs growth at a normal temperature, which provides good crystallinity as compared with LT-GaAs. Therefore, the mobility of carriers is high and the carrier life can be shortened since the produced carrier arrives fast at the n-type layer from the absorption layer. Moreover, the absorption layer serving as an electric field application layer is thin, thereby enabling an operation at a low voltage. In addition, carrier capture of the defect level by an As cluster is not used, resulting in less heat production and good film quality. Since variations as is often the case with LT-GaAs are less, the element characteristics are stable and the manufacturing yield is high. Conventionally, although a photoconductive element for generating THz exhibits excellent characteristics, the excitation efficiency cannot be increased due to a thin absorption layer. This embodiment of a lateral incidence type provides longer absorption, resulting in sufficient efficiency.

It should be noted that although an n-i-n structure is shown here by way of example, a p-i-n structure or m-i-n (metal-intrinsic-n-type) using Schottky junction may be employed to apply a reverse electric field. The composition and the thickness of the layer are not limited to the illustration provided herein.

Fifth Embodiment

According to a fifth embodiment of the present invention, there is provided a vertical electric field application type photoconductive element without a transfer process as in the first embodiment.

Figure 7:
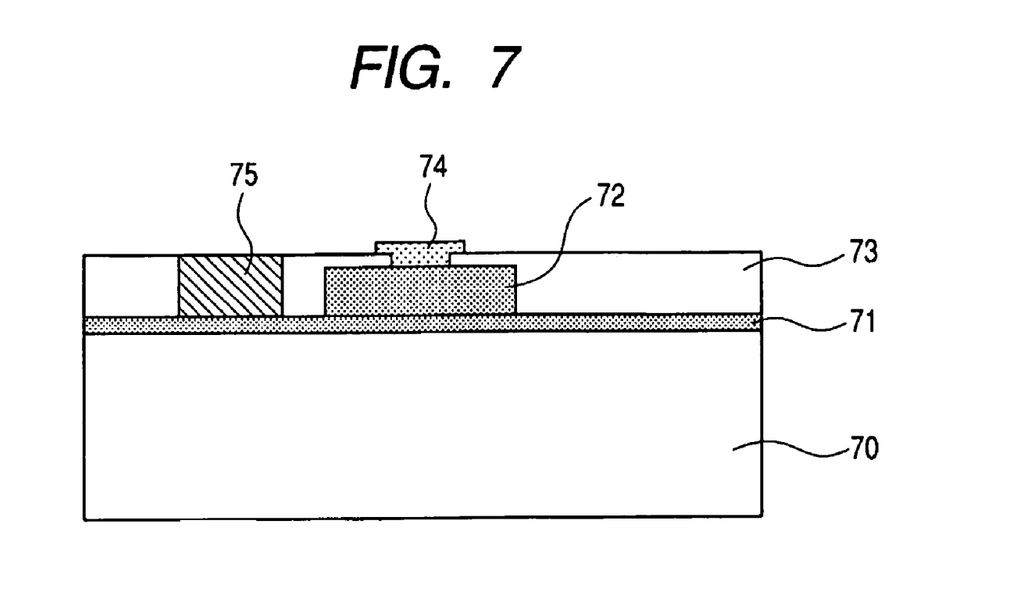
FIG. 7 is a cross sectional view of a photoconductive element portion according to a fifth embodiment of the present invention.

FIG. 7 shows a cross sectional view thereof. A semi-insulating GaAs 70 is used as a substrate. An n-type Al0.08 Ga0.92 As layer 71 and an LT-GaAs layer 72 for making electrode contact are epixitally grown using the MBE method. An insulating layer 73 and an upper electrode 74 are similar to corresponding ones in the first embodiment.

As for a lower electrode, the n-type layer 71 is highly doped to attain a metal-like operation, and an embedded electrode 75 realizes contact. The electrode 75 is configured such that an alloy electrode is composed of AuGe/Ni/Au at the portion in contact with the n-type AlGaAs and that the thickness is increased by Au plating. The contact layer is composed of AlGaAs in order to reduce absorption of light for excitation.

The photoconductive element configured as described above may be used alone. Alternatively, it may be configured as an integrated device as in the first to third embodiments. In this method without using transferring, the manufacturing process can be significantly simplified.

Sixth Embodiment

Figure 8:
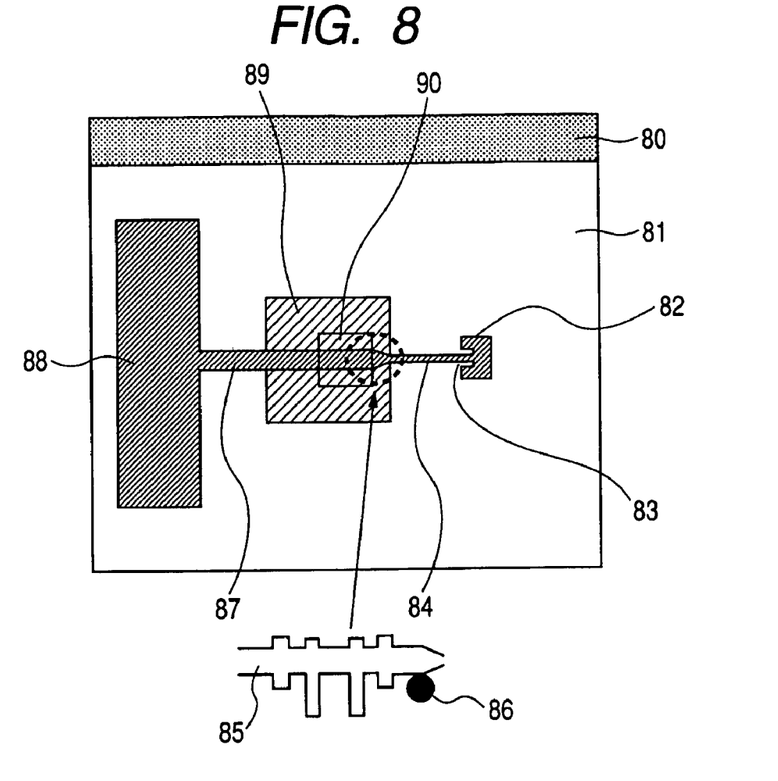
FIG. 8 is a plan view of an integrated device according to a sixth embodiment of the present invention.

FIG. 8 shows a plan view of an integrated device including a photoconductive element according to a sixth embodiment, a transmission path for an electromagnetic wave, and an antenna according to this embodiment.

A surface of a substrate 81 is coated with an Au thin film serving as a ground electrode and BCB having a thickness of 3 µm as a whole. A partial region 80 is free from BCB in order to make a ground. electrode. An LT-GaAs thin film 89 of a 1 mm square is transferred as in the first embodiment. A partial region 90 is provided with a window of BCB of a 500 µm square to expose a surface of the LT-GaAs thin film. An upper electrode 88 is provided such that a bias can be applied to a surface of LT-GaAs from the window region 90 through a Ti-Au line 87 having a width of 20 µm. A microstrip line 84 having a width of 5 µm for transmitting a terahertz electromagnetic wave generated by irradiating LT-GaAs with a short pulse laser beam is provided with a characteristic impedance adjusted to about 70 Ω. A patch antenna 82 approximately 90 µm square is provided for radiating a terahertz electromagnetic wave propagating through the microstrip line into space. A cut 83 is formed for impedance matching such that a feed point from the transmission path attains a depth of about 30 µm with respect to the end surface of the antenna.

A laser beam is applied to a spot of about 5 µm in the vicinity of the upper electrode of LT-GaAs, as denoted by a position 86 in the enlarged view. A part of the upper electrode may be provided with a. low-pass filter 85 for preventing propagation of a high frequency electromagnetic wave to an electrode pad 88, as shown in the enlarged view in FIG. 8. A part of the Ti/Au line 87 in the vicinity of the position 86 for conducting the laser beam irradiation may be provided with a cut or a protrusion for improving generation efficiency.

Figure 9:
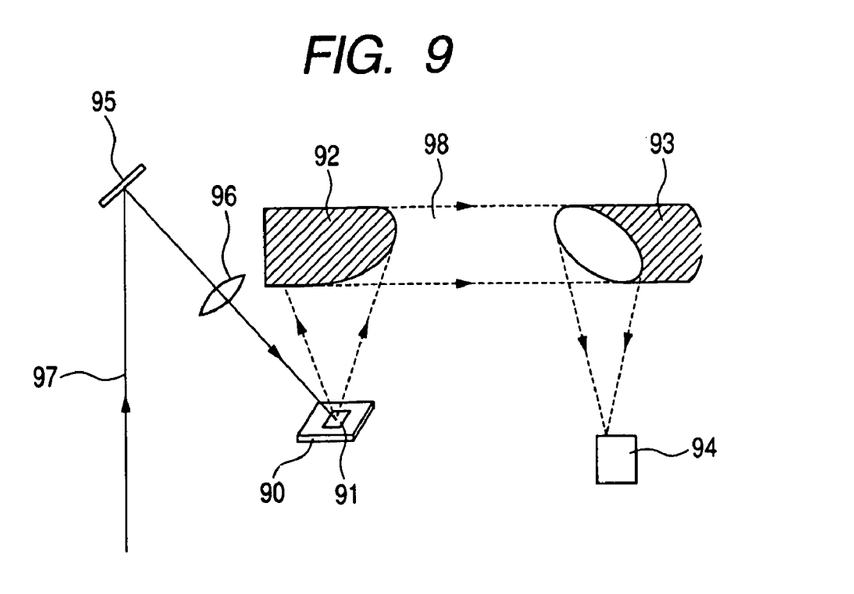
FIG. 9 shows an optical system according to the sixth embodiment of the present invention.

Sensing using a terahertz electromagnetic wave can be driven in the same way as the embodiments described above. An exemplary optical system using this device is shown in FIG. 9. A photoconductive element portion 91 of an integrated device 90 according to this embodiment is irradiated with a beam 97 from a femto-second laser through a reflecting mirror 95 and a lens 96. A terahertz electromagnetic wave generated from the integrated device 90 propagates through space, as shown by 98, through two parabolic mirrors 92 and 93, and is then received by a detector 94. Here, the femto-second laser beam may be branched and propagate through a delay system (not shown) to the detector 94 for the well-known coherent detection (time region spectrum detection or the like).

Here, impedance matching between a transmission line for a terahertz waveform and an antenna is performed so that the electromagnetic wave can radiate into space efficiently, thereby improving sensitivity in sensing an object on a transmission line as described in the first embodiment and the like.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2004-223656 filed on Jul. 30, 2004 and Japanese Patent Application No. 2005-025210 filed on Feb. 1, 2005, which are hereby incorporated by reference herein.

The invention claimed is:

1. An optical semiconductor device comprising:
a semiconductor film having photoconductive properties, the semiconductor film generating carriers by absorbing light at a light absorption edge of the semiconductor film; and
a pair of electrodes for applying an electric field to the semiconductor film causing the carriers to move, the pair of electrodes sandwiching the semiconductor film in a film thickness direction and having a propagating portion extending in a direction opposite the light absorption edge for propagating an electromagnetic wave generated from the semiconductor film by movement of the carriers,
wherein the propagating portion is in contact with the semiconductor film and serves as an antenna for radiating into space the electromagnetic wave generated from the semiconductor film, the electromagnetic wave having a frequency in a frequency region of 30 GHz or more and 30 THz or less.

2. An optical semiconductor device according to claim 1, wherein the pair of electrodes are arranged so as to interpose the semiconductor film in the direction perpendicular to the surface of the semiconductor film.

3. An optical semiconductor device according to claim 1, wherein the semiconductor film is a III-V semiconductor film.

4. An optical semiconductor device according to claim 1, wherein overlaid on at least one surface of the semiconductor film is a semiconductor material having a different type of conductivity and a different energy band gap than the semiconductor film.

5. An optical semiconductor device according to claim 1, wherein a transmission path for propagating the electromagnetic wave generated from the semiconductor film is continuously formed, and a metal constituting the transmission path is electrically connected to at least one electrode of the pair of electrodes.

6. An optical semiconductor device according to claim 1, further comprising an optical waveguide for applying light incident on a side surface of the semiconductor film to the region of the semiconductor film to which the electric field is applied.

7. An optical semiconductor device according to claim 2, wherein the electromagnetic wave is generated from the semiconductor film by conducting photoirradiation from above an upper side of the device through spatial propagation to a region of the semiconductor film in a vicinity of an electrode of the pair of electrodes that is arranged toward the upper side of the device relative to a second electrode of the pair of electrodes.

* * * * *